US00PP08469P

United States Patent [19]

Delbard

[11] Patent Number: Plant 8,469

[45] Date of Patent: Nov. 23, 1993

[54] ROSE PLANT—DELORO VARIETY

[75] Inventor: Georges Delbard, Commentry, France

[73] Assignee: Societe Civile Agricole Pèpiniéres et Roseraies Georges Delbard, Commentry, France

[21] Appl. No.: 965,696

[22] Filed: Oct. 23, 1992

[51] Int. Cl.[5] ..... A01H 5/00
[52] U.S. Cl. ..... Plt./18
[58] Field of Search ..... Plt./18

[56] References Cited

U.S. PATENT DOCUMENTS

P.P. 8,093 1/1993 Meillard ..... Plt. 18

*Primary Examiner*—Howard J. Locker
*Assistant Examiner*—E. F. McElwain
*Attorney, Agent, or Firm*—Burns, Doane, Swecker & Mathis

[57] ABSTRACT

A new and distinct variety of Hybrid Tea rose plant is provided which abundantly forms attractive double flowers which are light pink in coloration. Such flowers are long lasting and comprise petals which detach cleanly. The plant exhibits an upright to bushy growth habit, forms semi-vigorous to vigorous vegetation, and is well suited for greenhouse forcing for cut flower production. Additionally, the plant is very resistant to diseases when grown under greenhouse conditions.

1 Drawing Sheet

SUMMARY OF THE INVENTION

The new variety of Hybrid Tea rose plant was created by artificial pollination wherein two parents possessing red blossoms were crossed which previously had been studied in the hope that they would contribute the desired characteristics. The female parent (i.e., the seed parent) of the new variety was the ARORESAS variety (U.S. Plant Pat. No. 6,670). The male parent (i.e., the pollen parent) was the Korlingo variety (U.S. Plant Pat. No. 5,846). The parentage of the new variety can be summarized as follows:

Aroresas × Korlingo.

The seeds resulting from the above pollination were sown and 270 small plantlets were obtained which were physically and biologically different from each other. Selective study resulted in the identification of a single plant of the new variety.

It was found through careful study that the new variety of the present invention can be characterized by the following combination of characteristics:

(a) from a physical point of view it forms bronze green mature wood, assumes an upright to bushy growth habit, and forms attractive long-lasting light pin double flowers having consistent petals which detach cleanly, and
(b) from the biological point of view it forms semi-vigorous to vigorous vegetation, produces flowers in abundance, exhibits the ability readily to be forced, and is very resistant to diseases when grown under greenhouse conditions.

The new variety well meets the needs of the horticultural industry and is particularly well suited for growing in the greenhouse for the production of attractive long-lasting pink cut flowers.

The new variety can be readily distinguished from other varieties in view of the combination of characteristics described herein. It exhibits long and relatively straight stems, rigid and substantially straight peduncles, an excellent ability to be forced under greenhouse conditions, and a long vase life for its distinctive pink blossoms.

The new variety has been found to undergo asexual propagation and can be readily reproduced by conventional routes, such as budding (i.e., eye grafting). This asexual reproduction as performed in France has demonstrated that the characteristics of the new variety are strictly transmissible from one generation to another and are firmly fixed.

The new variety has been named the Deloro variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass at Hyéres (Var), France.

DETAILED DESCRIPTION

Figures 1, 2, 3, 4, 5, 6, 7, 8, 9, 10, 11, 12, 13, 14, 15, 16:
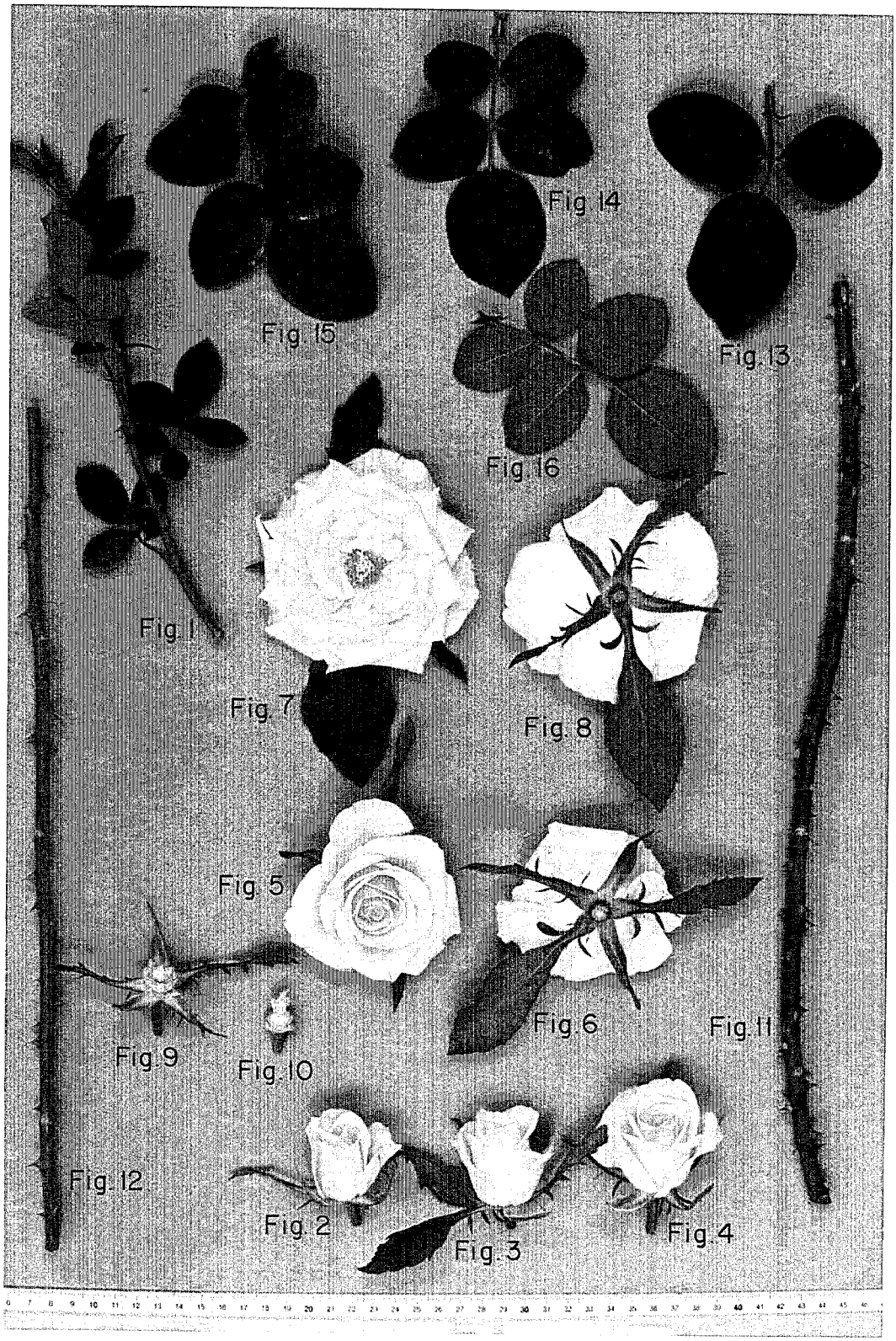
FIG. 1 illustrates a specimen of a young shoot.
FIG. 2 illustrates a specimen of a floral bud at the opening of the sepals.
FIG. 3 illustrates a specimen of a floral bud at the opening of the petals.
FIG. 4 illustrates a specimen of a flower in the course of opening.
FIG. 5 illustrates a specimen of an open flower — plan view — obverse.
FIG. 6 illustrates a specimen of an open flower — plan view — reverse.
FIG. 7 illustrates a specimen of a fully open flower — plan view — obverse.
FIG. 8 illustrates a specimen of a fully open flower — plan view — reverse.
FIG. 9 illustrates a specimen of a floral receptacle showing the arrangement of the stamens and pistils.
FIG. 10 illustrates a specimen of a floral receptacle showing the arrangement of the pistils (sepals and stamens removed)
FIG. 11 illustrates a specimen of a flowering stem.
FIG. 12 illustrates a specimen of a main branch.
FIG. 13 illustrates a specimen of a leaf with three leaflets — plan view — upper surface.
FIG. 14 illustrates a specimen of a leaf with five leaflets — plan view — upper surface.
FIG. 15 illustrates a specimen of a leaf with seven leaflets — plan view — upper surface.
FIG. 16 illustrates a specimen of a leaf with five leaflets — plan view — under surface.

The chart used in the identification of the colors is that The Royal Horticultural Society (R.H.S. Colour Chart). The description is based on the observation of plants grown under glass at Hyères (Var), France. The coloration in common terms sometimes also is provided.

Class: Hybrid Tea.

Plant:

*Height.*—Plants which were pruned at a height of 1 m. produce floral stems having a length of approximately 50 to 100 cm., and an average length of approximately 70 cm.

*Habit.*—Upright to bushy.

Branches:

*Color.*—Young shoots: when approximately 20 cm. long, exhibit an anthocyanin coloration, Greyed-Purple Group 184B. Floral stems: Yellow-Green Group 146A. Mature wood: Green Group 137C.

Thorns.—Configuration: concave to flat on upper surface and deep concave on lower surface. Quantity: Very few which are 5 mm. or less in length, and an average number which are greater than 5 mm. in length. Length: approximately 6.5 mm. on average on floral stems and approximately 6.5 mm. on average on mature wood, and commonly range from about 4 to 7 mm. in length in each instance. Color: when present on a shoot approximately 20 cm. long are Greyed-Purple Group 184A; when present on floral stems are yellow-green with bronze coloration, Yellow-Green Group 152D; and when present on mature wood are brownish, Greyed-Orange Group between 166B and 166C.

*Leaflets.*—Number: commonly 3, 5, and 7. Size: medium. Shape: as illustrated, and in cross section are convex. Serration: present. General appearance: glossiness on the upper surface of the leaflets is very week. Petiole color on young shoot: Greyed-Purple Group 183B on upper surface and Greyed-Purple Group 187B on under surface. Petiole color on floral stem: Yellow-Green Group 146B on upper surface and Yellow-Green Group 146A with bronze coloration on under surface. Petiole color on mature wood: Yellow-Green Group 146B on upper surface and Yellow-Green Group 146A on under surface. Petiole length of terminal leaflet: approximately 13 to 20 mm., approximately 18 mm. on average, and a standard deviation of 2 mm. Terminal leaflet length: approximately 39 to 72 mm., approximately 55 mm. on average, and a standard deviation of 6 mm. Terminal leaflet width: approximately 27 to 48 mm., approximately 39 mm. on average, and a standard deviation of 6 mm. Terminal leaflet shape at base: obtuse to rounded with a very weak undulation of the margin. Leaflet color of young shoot: Yellow-Green Group 146A with bronze coloration on upper surface and Greyed-Orange Group 174A with purple coloration of Greyed-Purple Group 184B on under surface. Leaflet color on floral stem: Yellow-Green Group 147A on upper surface and Yellow-Green Group 147B on the under surface. Leaflet color of mature wood: Yellow-Green Group 147A on upper surface and Yellow-Green Group 147B on under surface.

Inflorescence:

*Number of flowers.*—Generally on per stem when grown under forced greenhouse conditions; however, sometimes in such forced culture the first axillary eyes below the flower develop and form approximately 3 to 5 flowers; and when grown outside in the landscape multiple flowers which number approximately 3 to 5 are produced in regular clusters.

*Peduncle.*—few haris or prickles are present and is Yellow-Green Group 145B in coloration when the petals open.

*Sepals.*—Configuration: long with medium to long extensions. Color: Green Group 139C to 139D on upper surface, and Yellow-Green Group 144A on under surface.

*Buds.*—Shape: ovate in longitudinal section just before the opening of the sepals.

*Flowers.*—Time: Medium to late to begin flowering. Shape: double. Diameter: medium to large, approximately 8.8 to 9.8 cm., and approximately 9.3 cm. on average with a standard deviation of 0.5 cm. Petal number: commonly approximately 32 to 42, and an average of approximately 35. Petal size (second row from outside): the length is approximately 40 to 50 mm. with a mean of approximately 44 mm., and a standard deviation of 3 mm.; and the width is approximately 46 to 54 mm. with a mean of approximately 52 mm., and a standard deviation of 2 mm. Petal shape: the first row of petals commonly exhibit a very broad obovate configuration, the undulation of the petal margin is average, and the reflexing of the margin at the bud stage is strong and the reflexing of the margin when the flower is open is very weak. Petal color (middle zone): on the inner side Red Group 49C to 49D, and on the outer side Red Group 55C which begins at the base as very light pink, Red Group 49C and 49D. Petal color (marginal zone): on the inner side Red Group 55D, and on the outer side Red Group 55C which begins at the base as very light pink, Red Group 49C and 49 D. Petal spot at base: small in size, on the inner side Yellow Group 4C, and on the outer side Yellow Group 4D. Stamens: Approximately 80 in number and are somewhat regularly arranged around the pistils. Filaments: medium in length and Yellow Group 6D in coloration. Anthers: medium in size, all open at approximately the same time, and the immature coloration is Orange Group 24C. Pollen: Normal in quantity and yellow in coloration. Pistils: approximately 80 in number. Styles: medium in length and pale yellow in coloration, Yellow Group 10D. Stigmas: Yellow Group 10A in coloration, and generally are present at about the same level as the anthers, but a few anthers may be higher. Hips: in longitudinal section they are in the shape of a pitcher, and approximately 2.2 mm. in diameter. Seeds: medium in size, approximately 20 to 25 in number, and average approximately 23 in number. Petal drop: petals detach celanly. Fragrance: very slight. Lasting quality: long.

Development:

*Vegetation.*—Semi-vigorous to vigorous.

*Blooming.*—Abundant and nearly continuous.

*Resistance to forcing.*—Very good.

*Resistance to diseases.*—Very good under greenhouse conditions, and is sensitive to mildew outside.

I claim:

1. A new and distinct variety of Hybrid Tea rose plant characterized by the following combination of characteristics:

(a) from a physical point of view it forms bronze green mature wood, assumes an upright to bushy growth habit, and forms attractive long-lasting light pink double flowers having consistent petals which detach cleanly, and (b) from the biological point of view forms semi-vigorous to vigorous vegetation, produces flowers in abundance, exhibits the ability readily to be forced, and is very resistant to diseases when grown under greenhouse conditions;

substantially as herein shown and described.

* * * * *